United States Patent [19]
Felix et al.

[11] Patent Number: 5,696,089
[45] Date of Patent: Dec. 9, 1997

[54] HISTIDINE SUBSTITUTED GROWTH HORMONE RELEASING FACTOR ANALOGS

[75] Inventors: Arthur Martin Felix, West Caldwell; Edgar Philip Heimer, Nutley, both of N.J.

[73] Assignee: Roche Vitamins Inc., Paramus, N.J.

[21] Appl. No.: 461,218

[22] Filed: Jun. 5, 1995

Related U.S. Application Data

[63] Continuation of Ser. No. 270,094, Jul. 1, 1994, abandoned, which is a continuation of Ser. No. 82,830, Jun. 25, 1993, abandoned, which is a continuation of Ser. No. 795,241, Nov. 15, 1991, abandoned, which is a continuation of Ser. No. 546,268, Jun. 29, 1990, abandoned.

[51] Int. Cl.$^6$ .............. A61K 38/25; C07K 14/60
[52] U.S. Cl. .............. 514/12; 530/324; 930/DIG. 559
[58] Field of Search .............. 514/12, 2; 530/324, 530/325; 930/120, 10, DIG. 822, DIG. 820, DIG. 800, DIG. 559

[56] References Cited

U.S. PATENT DOCUMENTS

| | | | |
|---|---|---|---|
| 4,025,499 | 5/1977 | Thomas | 530/333 |
| 4,517,181 | 5/1985 | Ling et al. | 514/12 |
| 4,518,586 | 5/1985 | Rivier et al. | 514/12 |
| 4,528,190 | 7/1985 | Vale, Jr. et al. | 514/12 |
| 4,529,595 | 7/1985 | Rivier et al. | 514/12 |
| 4,562,175 | 12/1985 | Chang et al. | 514/12 |
| 4,563,352 | 1/1986 | Rivier et al. | 514/12 |
| 4,585,756 | 4/1986 | Brazeau, Jr. et al. | 514/12 |
| 4,595,676 | 6/1986 | Spiess et al. | 514/12 |
| 4,605,643 | 8/1986 | Bohlen et al. | 514/12 |
| 4,610,976 | 9/1986 | Bohlen et al. | 514/12 |
| 4,617,149 | 10/1986 | Di Marchi et al. | 570/324 |
| 4,618,598 | 10/1986 | Conn | 514/6 |
| 4,622,312 | 11/1986 | Felix et al. | 514/12 |
| 4,626,523 | 12/1986 | Vale, Jr. et al. | 514/12 |
| 4,628,043 | 12/1986 | Spiess et al. | 514/12 |
| 4,649,039 | 3/1987 | Garlick et al. | 424/1.1 |
| 4,649,131 | 3/1987 | Felix et al. | 514/12 |
| 4,689,318 | 8/1987 | Kaiser et al. | 514/12 |
| 4,703,035 | 10/1987 | Rivier et al. | 514/12 |
| 4,728,726 | 3/1988 | Rivier et al. | 530/324 |
| 4,732,972 | 3/1988 | Felix et al. | 530/324 |
| 4,734,399 | 3/1988 | Felix et al. | 514/12 |
| 4,783,524 | 11/1988 | Larsen et al. | 530/350 |
| 4,784,987 | 11/1988 | Rivier et al. | 514/12 |
| 4,914,189 | 4/1990 | Schally et al. | 530/324 |

FOREIGN PATENT DOCUMENTS

| | | |
|---|---|---|
| 23075/84 | 1/1984 | Australia. |
| 105759 | 10/1983 | European Pat. Off.. |
| 117034 | 1/1984 | European Pat. Off.. |
| 121764 | 3/1984 | European Pat. Off.. |
| 138416 | 9/1984 | European Pat. Off.. |
| 177819 | 9/1985 | European Pat. Off.. |
| 0177819 | 4/1986 | European Pat. Off.. |
| 0188214 | 7/1986 | European Pat. Off.. |
| 216517 | 8/1986 | European Pat. Off.. |
| 264 750 | 4/1988 | European Pat. Off.. |
| 292334 | 5/1988 | European Pat. Off.. |
| 90/08776 | 8/1990 | European Pat. Off.. |
| WO 90/15821 | 12/1990 | European Pat. Off.. |
| 8907113 | 8/1989 | WIPO. |

OTHER PUBLICATIONS

Frohman et al, The American Society for Clinical Investigation, Inc., vol. 83, pp. 1533–1540, (May 1989).
Rudinger, Peptide Hormones, pp. 1–7, (Jun. 1976).
Dayhoff, Margaret, Atlas of Protein Sequence and Structure, Washington: Nat. Biomed Res. Found. 1972, vol. 5, p. 96.
Schulz et al, Principles of Protein Structure. New York: Springer–Verlag. 1979, pp. 14–16.
Smith, J.A. and Rivier, J.E., *Peptides: Chemistry and Biology*, Proceedings of the American Peptide Symposium, Cambridge, Jun. 16–21, 1991.
Marshall, G.R., *Peptides: Chemistry and Biology*, Proceedings of the 10th American Symposium, St. Louis, May 23–28, 1987.
Derwent Abstract No. 88–111768/16 (1988).
Science, 218(5), 585 (1982).
Nature, 300, 276 (1982).
Proc. Natl. Acad. Sci. USA 79, 7909 (1982).
J. Clin. Endo. Metab. 57(3), 677 (1983).
Unlisted Drugs, 35(3), 41 (1983).
Nature, 303, 532 (1983).
Biochem. Biophys. Res. Comm., 119(1), 265 (1984).
Medical World, Mar. 12, 1984, p. 37.
Proc. 7th Inter. Cong. Endo, Quebec City, Jul. 1–7, 1984, paper N–873.

(List continued on next page.)

*Primary Examiner*—Jeffrey E. Russel
*Attorney, Agent, or Firm*—George W. Johnston; Dennis P. Tramaloni; Alan P. Kass

[57] ABSTRACT

Novel growth hormone releasing factor analogs are presented having the formula:

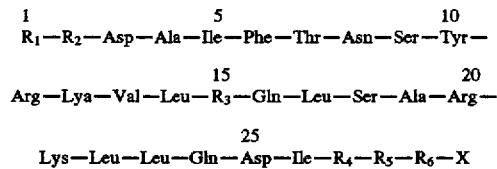

wherein $R_1$ is His, 3-MeHis, desNH$_2$His, Tyr, or desNH$_2$Tyr; $R_2$ is Val, Leu, or Ile; $R_3$ is Ala; $R_4$ is Met, Leu, Ile, or Nle; $R_5$ is Ser or Asn; $R_6$ is an amino acid residue sequence selected from Arg-Gln-Gln-Gly-Glu-Ser-Asn-Gln-Glu-Arg-Gly-Ala-Arg-Ala-Arg-Leu or fragments thereof where the fragment is reduced in number by one to fifteen amino acid residues from the amino acid residue which carries the substituent X; and X is either OH or NH$_2$, and the pharmaceutically acceptable acid or base addition salts thereof. The novel growth hormone releasing factor analogs demonstrate enhanced potency for the released growth hormone, have enhanced enzymatic stability, and can be administered to a subject having a deficiency of growth hormone or for improvement of growth performance in livestock.

13 Claims, No Drawings

OTHER PUBLICATIONS

Proc. 7th Inter. Cong. Endo, Quebec City, Jul. 1–7, 1984, Abstracts N–885, N–887/889, N–891/893, N–849.
Biochem. Biophys. Res. Comm. 123(2), 497 (1984).
Biochem. Biophys. Res. Comm. 123(2), 854 (1984).
New York Times. Apr. 17, 1988, p. C1.
Molecular Endocrinology, 3(10), 1529 (1989).
Principles of Biochemistry, 5th Ed., pp. 1126–1129 (not dated).
*Life Science*, 46(7), 999 (1990).
Derwent Abstracts of WO 90/15821 (Dec. 27, 1990).
Frohman et al., The American Society for Clinical Investigation, Inc. vol. 83, pp. 1533–4015 (1989).
Rudiger Peptide Hormones, pp. 1–7 (1976).

HISTIDINE SUBSTITUTED GROWTH HORMONE RELEASING FACTOR ANALOGS

This is a continuation of application Ser. No. 08/270,094, filed Jul. 1, 1994, now abandoned, which is a continuation of application Ser. No. 08/082,830, filed Jun. 25, 1993, now abandoned, which is a continuation of Ser. No. 07/795,241, filed Nov. 15, 1991, now abandoned, which is a continuation of Ser. No. 07/546,268, filed Jun. 29, 1990, now abandoned.

FIELD OF THE INVENTION

This invention relates to analogs of human growth hormone releasing factor and to fragments thereof. The pharmaceutical compositions of the invention can be used to treat a variety of growth hormone related problems in human beings and for performance enhancement in animals.

BACKGROUND OF THE INVENTION

Growth hormone releasing factor (GRF) has been isolated from human islet cell tumor and structurally characterized by Guillemin and co-workers, *Science*, 218, 585–587 (Nov. 5, 1982) and Rivier and co-workers, *Nature*, 300, 276–278 (1982). The isolation and characterization of GRF, while sought for decades, was previously unsuccessful due to its presence in very small quantities. Human hypothalamic growth hormone releasing factor (hGRF) has now been found to have the same structure as GRF isolated from islet cell tumor. Bohlen et al, *Biochem. and Biophysl Res. Comm.*, 114(3), 930–936 (1983).

Rivier and co-workers, Id., have described the structure of GRF (1-44) and GRF (1-40), respectively, and shown that GRF is specific for the release of growth hormone. These two forms of GRF are identical at the amino ($NH_2$) terminal but differ in the termination point of the carboxy (COOH) terminus. GRF (1-44) is further distinguished in having an amide group at the carboxy terminus.

Rivier and Vale et al, Id., have shown that the biological activity of GRF resides in the $NH_2$-terminal portion of the molecule and full intrinsic activity and potency was demonstrated with GRF(1-29)-$NH_2$ in vitro.

Lance et al, *Biochemical and Biophysical Research Communications*, 119(1), 265–272 (1984) have shown that GRF (1-29)-$NH_2$ with substitutions of selected amino acids at positions 1, 2 and 3 cause enhanced release of growth hormone (GH) in both pig and rat in vivo.

Growth in animals is presumably regulated by a cascade of bio-regulatory molecules. The hypothalamus produces GRF which induces pituitary release of growth hormone. Small quantities of GRF have been found to cause substantial pituitary release of growth hormone into the blood. Thus, GRF has great therapeutic utility in those instances where growth hormone is indicated. For example, GRF may be used in the treatment of hypopituitary dwarfism, diabetes due to growth hormone production abnormalities, enhancement of wound healing, treatment of burns, retardation of the aging process or osteoporosis or bone healing. Similarly, GRF has utility in the agricultural field. Examples of agricultural uses include, enhanced meat production of fowl or animals raised for food such as pigs, cattle or the like to permit earlier marketing or to produce larger animals for similar time on feed or improve the lean to fat ratios. GRF may also stimulate milk production in dairy cows and egg production in chickens.

The successful isolation of GRF was due partly to the discovery that pancreatic tumors associated with acromegaly ectopically produced large quantities of GRF. Three forms of GRF, consisting of peptides homologous from the amino terminus of 44, 40 and 37 amino acids, were isolated.

The 44 amino acid amidated form of GRF is considered to be the parent molecule. A wide variety of synthetic analogs have been produced. They consist of biologically active fragments of the original polypeptide which incorporate various amino acid substitutions. The changes have been specifically engineered to often yield synthetic analogs with biological properties superior to those of the parent molecule. Generally, linear peptides are very flexible molecules and lack a well-defined conformation. Each amino acid in a linear peptide is exposed to the surrounding milieau resulting in greater susceptibility to enzymatic and chemical degradation.

Accordingly, the desire is to engineer GRF analogs which exhibit maximum biological activity in terms of, for example, potency, effectiveness, and stability together with resistance to enzymatic and chemical degradation.

SUMMARY OF THE INVENTION

The present invention relates to compounds of the formula:

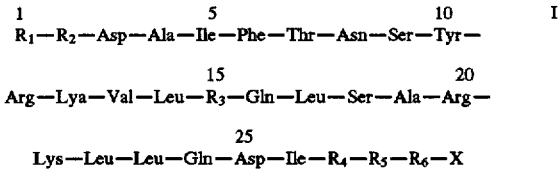

wherein $R_1$ is His, 3-MeHis, desNH$_2$His, Tyr, or desNH$_2$Tyr; $R_2$ is Val, Leu, or Ile; $R_3$ is Ala; $R_4$ is Met, Leu, Ile, or Nle; $R_5$ is Ser or Asn; $R_6$ is an amino acid sequence selected from Arg-Gln-Gln-Gly-Glu-Ser-Asn-Gln-Glu-Arg-Gly-Ala-Arg-Ala-Arg-Leu or fragments thereof where the fragment is reduced in number by one to fifteen amino acid residues from the amino acid residue which carries the substituent X; and X is either OH or $NH_2$, and the pharmaceutically acceptable acid or base addition salts thereof.

Pharmaceutical compositions in accordance with the invention include such analogs which are between twenty-nine (29) and forty-four (44) residues in length dispersed in a pharmaceutically or veterinary acceptable liquid or solid carrier. Such pharmaceutical compositions can be used in clinical medicine, both human and veterinary, for administration for therapeutic and/or diagnostic purposes. Moreover, they can be used to promote the growth of warm and cold-blooded animals. They can also be used to treat growth related disorders and improve growth performance in warm and cold-blooded animals.

The GRF peptides of this invention are useful in methods for stimulating the release of growth hormone from the pituitary for use in the treatments described above.

DETAILED DESCRIPTION OF THE INVENTION

As used herein, the term "GRF" means human growth hormone releasing factor, a polypeptide having the amino acid sequence (*Science*, 281, 585, Nov. 5, 1982)

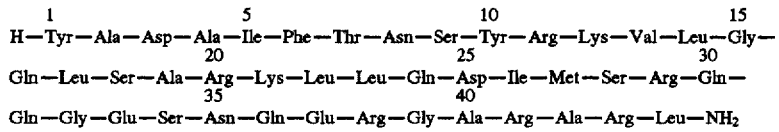

or biologically active fragments having at least the first 29 amino acids of the full polypeptide and displaying growth hormone releasing activity. In accordance with conventional representation, the amino group at the N-terminus appears to the left and the carboxyl group at the C-terminus to the right. Amino acid is taken to mean one of the naturally occurring amino acids typically found in proteins comprising Gly, Ala, Val, Leu, Ile, Ser, Thr, Lys, Arg, Asp, Asn, Glu, Gln, Cys, Met, Phe, Tyr, Pro, Trp, and His. Nle means norleucine. Where the amino acid residue has isomeric forms, it is the L-form of the amino acid that is represented unless otherwise expressly indicated. The suffixes "—OH" and "—NH$_2$" following "GRF" refer to the free acid and amide forms of the polypeptide, respectively. In the event neither suffix is used, the expression is intended to encompass both forms. Analogs of GRF are indicated by setting forth the substituted amino acid in brackets before "GRF"; for example, "[His$^1$, Ala$^{15}$]-GRF" indicates a polypeptide having an amino acid sequence corresponding to GRF in which a histidine residue has been substituted for the tyrosine residue at position 1 and an alanine residue has been substituted for the glycine residue at position 15. Numbers in parentheses following "GRF" indicate fragments of the full polypeptide by giving the position numbers of the amino acid residues; for example, GRF (1-29) indicates a fragment having the first 29 amino acids of the full sequence.

The invention relates to compounds of the formula:

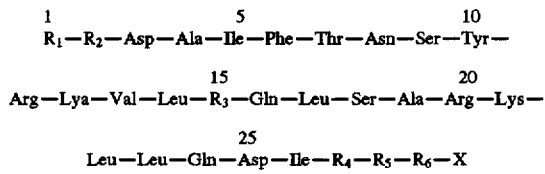

wherein $R_1$ is His, 3-MeHis, desNH$_2$His, Tyr, or desNH$_2$Tyr; $R_2$ is Val, Leu, or Ile; $R_3$ is Ala; $R_4$ is Met, Leu, Ile, or Nle; $R_5$ is Ser or Asn; $R_6$ is an amino acid sequence selected from Arg-Gln-Gln-Gly-Glu-Ser-Asn-Gln-Glu-Arg-Gly-Ala-Arg-Leu or fragments thereof where the fragment is reduced in number by one to fifteen amino acid residues from the amino acid residue which carries the substituent X; and X is either OH or NH$_2$, and the pharmaceutically acceptable acid or base addition salts thereof.

Pharmaceutical compositions in accordance with the invention include such analogs which are between twenty-nine (29) and forty-four (44) residues in length dispersed in a pharmaceutically or veterinary acceptable liquid or solid carrier. Such pharmaceutical compositions can be used in clinical medicine, both human and veterinary, for administration for therapeutic and for diagnostic purposes. Moreover, they can be used to promote the growth of warm and cold-blooded animals.

This invention is based on the discovery that the tyrosine residue at position 1 and/or the alanine residue at position 2 and the glycine residue at position 15 of the GRF molecule can be replaced by a different appropriately selected amino acid producing a GRF analog having enhanced biological potency for stimulating the release of growth hormone from the pituitary. Additionally, the methionine residue at position 27 and/or the serine residue at position 28 can also be replaced in the same manner, also producing a GRF analog having enhanced biological potency.

Various methods well known in the art may be used to select a particular amino acid for substitution in GRF at a particular position. One such method is to select a substitute amino acid so as to enhance the amphiphilic character and helical structure of the resulting polypeptide as demonstrated by helicity and hydropathicity analysis. The resultant peptides may bind more efficiently to the receptor and may be more stable to proteolytic breakdown thereby enhancing biological potency. Helicity and hydropathicity analyses are done by conventional methods known in the art.

In accordance with the invention substitutions of appropriately selected amino acid residues at positions 1 and/or 2 and 15 of GRF (1-29) have enhanced biological activity and enzyme resistance. Additional substitutions of appropriately selected amino acid residues at positions 27 and/or 28 of the GRF molecule concomitant to the substitution at the 1 and/or 2 and 15 positions produce a multisubstituted GRF analog yielding peptides having increased biological potency in effecting the release of GRF by the pituitary. Selected amino acids for substitution at the appropriately selected positions include but are not limited to tyrosine, desNH$_2$tyrosine, alanine, leucine, isoleucine, methionine, valine, asparagine, serine, norleucine, histidine, desNH$_2$histidine, and 3-methylhistidine.

Further, the acid or amide of the 29 amino acid GRF (1-29) or a GRF analog greater than about 29 amino acids and less than 44 amino acids in length in addition to the substitution at the 1, 2, 15, 27 and 28 positions have enhanced biological activity and increased enzyme resistance.

Representative compounds of the present invention include:

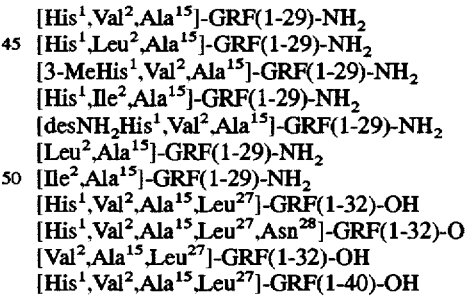

Although the modifications described are for the sequence comprising human growth hormone releasing factor, hGRF, similar modifications may be made to porcine growth hormone releasing factor, pGRF; bovine growth hormone releasing factor, bGRF; ovine growth hormone releasing factor, oGRF; and caprine growth hormone releasing factor, cGRF.

The polypeptides of this invention can be prepared by many procedures including, but not limited to, recombinant DNA methods, solid phase peptide synthesis techniques, or solution phase peptide synthesis techniques.

Using known techniques of DNA recombination, a DNA sequence containing the structural code for GRF could be inserted into a replicable expression vehicle under the control of appropriate control elements including a promoter-operator sequence and a sequence coding for a ribosome binding site. The expression vehicle would then be used to transform a host microorganism, such as a bacterium, which would be grown up and subjected to conditions under which it would express GRF. It will be recognized by those of ordinary skill in the art that only natural amino acids can be introduced by recombinant technology. In those instances where non-naturally occurring amino acids are substituted in the GRF analogs, recombinant DNA techniques can be utilized to prepare the natural amino acid residues which could then be coupled with fragments containing non-naturally occurring amino acids by procedures well known in the art.

Peptides may be prepared using solid phase synthesis, such as that described by Merrifield, *J. Am. Chem. Soc.*, 85, 2149 (1963), although other equivalent chemical syntheses known to one of ordinary skill may be used. Solid phase synthesis is commenced from the C-terminal end of the peptide by coupling a protected amino acid via a benzyl ester linkage to a chloromethylated resin or a hydroxymethyl resin or via an amide bond to a benzhydrylamine (BHA) resin or methylbenzhydrylamine (MBHA) resin. The resins are available commercially and their preparation is known by one of ordinary skill in the art.

The acid form of the novel analogs may be prepared by the solid phase peptide synthesis procedure using a benzyl ester-resin or phenylacetamidomethyl-resin as a solid support. The polypeptide may be purified by preparative high performance liquid chromatography (HPLC) and then shown to be homogeneous by analytical HPLC, isoelectric focusing and high voltage thin layer electrophoresis. Amino acid analysis may be performed so as to confirm the expected amino acid composition. The corresponding amides may be produced by using benzhydrylamine or methylbenzhydrylamine resin as the solid support for solid phase peptide synthesis. Those skilled in the art will recognize that when the BHA or MBHA resin is used, treatment with anhydrous HF to remove the polypeptide from the solid support results in a polypeptide having a terminal amide group.

The C-terminal amino acid, for example, Arg is protected at the $N^\alpha$-amino and side chain guanidino positions by appropriately selected protecting groups, in the case of Arg by t-butyloxycarbonyl (Boc) and p-toluenesulfonyl (Tos), respectively. The Boc-Arg(Tos)-OH can be first coupled to the benzhydrylamine resin using dicyclohexylcarbodiimide (DCC) at about 25° C. for 2 hours with stirring. Following the coupling of the Boc protected amino acid to the resin support, the α-amino protecting group is removed, using trifluoroacetic acid (TFA) in methylene chloride or TFA alone. The deprotection is carried out at a temperature between about 0° C. and room temperature.

After removal of the α-amino protecting group, the remaining Boc-protected amino acids are coupled step-wise in the desired order or as an alternative to adding each amino acid separately in the synthesis, some may be activated prior to its addition to the solid phase synthesizer. The selection of an appropriate coupling reagent is known to one of ordinary skill in the art. Particularly suitable is DCC.

Each protected amino acid or amino acid sequence is introduced into the solid phase reactor in excess, and the coupling may be carried out in a medium of dimethylformamide (DMF) or methylene chloride ($CH_2Cl_2$) or mixtures thereof. In cases where incomplete coupling occurs, the coupling procedure is repeated before removal of the $N^\alpha$-amino protecting group prior to the coupling of the next amino acid. The success of the coupling reaction at each stage of synthesis may be monitored by procedures well known in the art. A preferred method of monitoring the synthesis is by the ninhydrin reaction. The coupling reactions can be performed automatically, for example, using a Vega 1000, a 250 or 296 Peptide Synthesizer or Applied Biosystems Model 430A or 431A Peptide Synthesizer.

Cleavage of the peptide from the resin can be effected using procedures well known in peptide chemistry. Reaction with hydrogen fluoride in the presence of scavengers such as p-cresol and dimethylsulfide at 0° C. for 1 hour may be followed by a second reaction with hydrogen fluoride in the presence of p-cresol for 2 hours at 0° C.

Purification of the polypeptides of the invention can be effected using procedures well known in peptide chemistry.

As previously indicated, the subject polypeptides may be purified using preparative HPLC; however, other known chromatographic procedures such as gel permeation, ion exchange and partition chromatography or counter-current distribution can also be employed.

The polypeptides of this invention have growth hormone releasing activity. Pharmaceutical compositions in accordance with the invention include analogs of about 29 to about 44 amino acids in length, or a nontoxic salt of any of these, dispersed in a pharmaceutically or veterinarily acceptable liquid or solid carrier. Such pharmaceutical compositions can be used for therapeutic or diagnostic purposes in clinical medicine, both human and veterinary. For example, they are useful in the treatment of growth-related disorders such as hypopituitary dwarfism and diabetes resulting from abnormalities in growth hormone production. Furthermore they can also be used to stimulate the growth or enhance feed efficiency of animals raised for meat production, to enhance milk production, and stimulate egg production.

Appropriate dosages of the polypeptides of the invention to be administered will vary somewhat depending on the individual subject and the condition being treated. The skilled worker will be able to determine appropriate dosages based on the known circulating levels of growth hormone associated with normal growth and the growth hormone releasing activity of the polypeptide.

Compounds of this invention induced release of growth hormone in vitro approximately three (3) fold greater than that of GRF-(1-44)-$NH_2$. Thus, these analogs can be administered in significantly lower dosages than if growth hormone releasing factor were given for the same purpose. As is well known in the art, treatment of growth-related disorders will necessitate varying dosages from individual to individual depending upon the degree of insufficiency of growth hormone production. Generally, a dosage range of from about 0.04 μg/kg/day to about 20.0 μg/kg/day (subcutaneous) based on body weight of the subject may be used to stimulate release of growth hormone. The dosage employed to stimulate growth activity in livestock will be significantly higher (per kg. of subject weight) than the dosages employed to restore normal growth in cases of growth hormone deficiencies such as pituitary dwarfism in humans. In livestock generally a dosage in the range of from about 0.4 μg/kg/day to about 30 μg/kg/day subcutaneously may be used to stimulate release of pituitary growth hormone.

Thus, there is provided in accordance with this invention a method of treating growth-related disorders characterized by insufficient production of growth hormone which comprises administering an amount of the analogs of this invention sufficient to stimulate the production of growth hormone to levels associated with normal growth.

Normal levels of growth hormone vary considerably among individuals and, for any given individual, levels of circulating growth hormone vary considerably during the course of a day. In adult humans, normal serum levels of growth hormone have been reported to vary from about 0 to about 10 nanograms/ml. In children, normal serum levels of growth hormone have been reported to vary from about 0 to about 20 nanograms/ml.

In order to treat hypopituitary dwarfism effectively with the described analogs, treatment is administered during the period of normal growth. In females, this period generally does not extend far beyond the onset of menses. Thus, treatment of females should be commenced approximately from the age of 12 to 16 years, depending upon the individual. In males, the stimulation of growth may be possible for a considerably longer period of time beyond puberty. Thus, effective treatment of males will normally be possible up to about 18 to 19 years of age and, in some individual cases, up to about 25 years.

There is also provided a method of increasing the growth rate of animals by administering an amount of the inventive GRF analog sufficient to stimulate the production of growth hormone at a level greater than that associated with normal growth.

The polypeptides of the invention can be administered in the form of human or veterinary pharmaceutical compositions which can be prepared by conventional pharmaceutical formulation techniques. Compositions suitable for oral, intravenous, subcutaneous, intramuscular, intraperitoneal or intranasal administration may be employed. A suitable dosage form for pharmaceutical use is from about 0.01 to about 0.5 mg of the compound of the invention, which may be lyophilized for reconstitution with sterile water or saline. The composition should be maintained at a pH below about 8.0 in order to maintain the stability of the analog. Serum albumin from the species being treated (e.g. human serum albumin in the case of humans, bovine serum albumin in the case of cows and so forth) may also be present together with other known pharmaceutical adjuvants.

The polypeptides of this invention describe GRF analogs which possess enhanced stability to enzymatic (dipeptidylpeptidase-IV) degradation.

The following examples are presented in order to illustrate the practice of this invention and are not to be construed as limiting the scope of the invention in any way. Unless otherwise stated, all parts and percents are given by weight and all temperatures are in degrees centigrade. Unless otherwise stated (as in the present tense), the examples below have been carried out as actually described.

In the examples, optically active protected amino acids in the L-configuration were employed except where specifically noted. The protected amino acids were examined by thin layer chromatography on silica gel G plates and developed with chlorine-TDM. Amino acid analysis was performed on a Waters Amino Acid Analyzer.

The following abbreviations are used in the examples to indicate various protecting groups and reagents.
BOC=t-butyloxycarbonyl
TOS=p-toluenesulfonyl
DCC=dicyclohexylcarbodiimide
BHA=benzhydrylamine
DMF=dimethylformamide
TFA=trifluoroacetic acid
EtOAc=ethyl acetate
$CH_2Cl_2$=methylene chloride
Bzl=benzyl
cHex=cyclohexyl
2Cz=2-chlorobenzyloxycarbonyl
Dcb=2,6-dichlorobenzyl
BOP=benzotriazol-1-yloxytris(dimethylamino) phosphonium hexafluorophosphate
PAM=phenylacetamidomethyl The analogs of this invention were prepared by sequential coupling of amino acids by a manual mode or by employing commercially available automated solid phase peptide synthesizers (for example, Vega 1000, 250 or 296 Peptide Synthesizer or the Applied Biosystems Model 431A or A Peptide Synthesizer). $N^\alpha$-Boc-amino acids were used in the synthesis.

Trifunctional amino acids were protected as $N^\alpha$-Boc-Arg(Tos)-OH, $N^\alpha$-Boc-His(Tos)-OH, $N^\alpha$-Boc-Lys(2Cz)-OH, $N^\alpha$-Boc-Ser(Bzl)-OH, $N^\alpha$-Boc-Thr(Bzl)-OH, $N^\alpha$-Boc-Asp(cHex)-OH and $N^\alpha$-Boc-Tyr(Dcb)-OH.

EXAMPLE 1

Preparation of [$His^1,Val^2,Ala^{15}$]-GRF(1-29)-$NH_2$

Boc-Arg(Tos)-benzhydrylamine resin (350.0 g, 0.43 mmol/g), as prepared in U.S. Pat. No. 4,622,312, was charged into the reaction vessel of a peptide synthesizer (Vega 296) and solid phase peptide synthesis was performed by the DCC procedure for a total of 26 cycles to give protected [$Ala^{15}$]-GRF(3-29)-BHA-resin. A 1 g portion of the peptide-resin was removed, charged into a reaction vessel and Boc-Val-OH and Boc-His(Tos)-OH were activated with the BOP reagent and added sequentially in a manual solid phase mode to give [$His^1,Val^2,Ala^{15}$]-GRF(1-29)-BHA-resin (1.02 g). The protected peptide resin (1 g) was treated with anhydrous HF (containing 10% propanethiol) for 2 h at 0°, evaporated at 0° (high-vac; CaO trap), triturated with EtOAc and extracted with TFA. The solvent was evaporated and the residue was triturated with anhydrous ether and dried to give 490 mg of crude peptide.

The crude material (490 mg) was dissolved in 25 mL of 0.025% TFA/$H_2O$, filtered (0.45 micron type HA Millipore filter) and loaded onto a Synchropak RP-P column (2.0 cm×50 cm). The column was eluted with (A) $H_2O$ (0.025% TFA)-(B) $CH_3CN$ (0.025% TFA) in a linear gradient from 20% (B) to 45% (B) in 90 minutes with a flow rate of 12 mL/min. Fractions were collected (1 min/fraction) and aliquots analyzed by the analytical HPLC system: (A) 0.1M $NaClO_4$ (pH 2.5)-(B) $CH_3CN$; 40% (B) to 55% (B) in 20 min at 1 mL/min, 0.2 AUFS, 206 nm. Column: Lichrosorb RP-8 5 micron. The product emerged in fractions 32–35 (semi-pure) and fractions 36–51 (side cuts) which were combined, evaporated and lyophilized to give semi-pure [$His^1,Val^2,Ala^{15}$]-GRF(1-29)-$NH_2$. Yield: 19 mg and 55 mg, respectively.

The semi-pure material (19 mg) was dissolved in 5 mL of 0.025% TFA/$H_2O$, centrifuged, filtered (0.35μ type HA Millipore filter) and loaded onto a 1×50 cm Nucleosil column. The column was eluted with (A) $H_2O$ (0.025% TFA)-(B) $CH_3CN$ (0.025% TFA) in a linear gradient from 20% (B) to 40% (B) $H_2O$ in 120 minutes with a flow rate of 3 mL/min. Fractions were collected (1 min/fraction) and aliquots analyzed by the analytical HPLC system. The product emerged in fractions 74–86 which were combined, evaporated and lyophilized to give pure [$His^1,Val^2,Ala^{15}$]-GRF(1-29)-$NH_2$. Yield: 10 mg.

The product was shown to be homogeneous by analytical HPLC and gave the expected amino acid composition after acid hydrolysis (Hydrolysis: 6N HCl, 110° C., 72h): Asp 2.96 (3); Thr 0.85 (1); Ser 2.92 (3); Glu 2.30 (2); Ala 3.00 (3); Val 1.84 (2); Met 1.05 (1); Ile 1.90 (2); Leu 4.43 (4); Tyr 0.83 (1); Phe 0.88 (1); Lys 2.19 (2); His 0.92 (1); Arg 3.19 (3). Confirmation of structure was provided by FAB mass spectroscopy. Calcd: $(M+H)^+$3374.0. Found: 3373.7.

EXAMPLE 2

Preparation of [His$^1$,Leu$^2$,Ala$^{15}$]-GRF(1-29)-NH$_2$

A 1 g portion of protected [Ala$^{15}$]-GRF(3-29)-BHA-resin was subjected to 2 cycles of solid phase peptide synthesis as in Example 1 to give 1.12 g of protected [His$^1$,Leu$^2$, Ala$^{15}$]-GRF(1-29)-BHA-resin. A 0.6 portion was cleaved with anhydrous HF to give 245 mg of crude peptide which was purified. (as in Example 1) and 25.4 mg of pure [His$^1$,Leu$^2$,Ala$^{15}$]-GRF(1-29)-NH$_2$ was obtained.

The product was shown to be homogeneous by analytical HPLC and gave the expected amino acid composition after acid hydrolysis (Hydrolysis: 6N HCl, 150° C., 1h): Thr 0.95 (1); Ser 2.92 (3); Tyr 1.12 (1). (Hydrolysis: 6N HCl, 110° C., 24h): Asp 2.91 (3); Glu 2.14 (2); Ala 3.00 (3); Met 0.99 (1); Leu 4.97 (5); His 0.92 (1); Lys 1.99 (2); Arg 3.04 (3). (Hydrolysis: 6N HCl, 110° C., 72h): Val 1.02 (1); Ile 2.05 (2); Phe 0.97 (1). Confirmation of structure was provided by FAB mass spectroscopy. Calcd: $(M+H)^+$3389.0. Found: 3388.8.

EXAMPLE 3

Preparation of [3-MeHis$^1$,Val$^2$,Ala$^{15}$]-GRF(1-29)-NH$_2$

A 1 g portion of protected [Ala$^{15}$]-GRF(3-29)-BHA-resin, as prepared in Example 1, was subjected to 2 cycles of solid phase peptide synthesis as in Example 1 to give 1.08 g of protected [3-MeHis$^1$,Val$^2$,Ala$^{15}$]-GRF(1-29)-BHA-resin. A 0.5 g portion was cleaved, extracted and purified as in Example 1 to give 11.5 mg of pure [3-MeHis$^1$,Val$^2$,Ala$^{15}$]-GRF(1-29)-NH$_2$.

The product was shown to be homogeneous by analytical HPLC and gave the expected amino acid composition after acid hydrolysis (Hydrolysis: 6N HCl, 110° C., 24h): Asp 2.90 (3); Thr 0.85 (1); Ser 3.00 (3); Glu 2.34 (2); Ala 3.00 (3); Val 1.69 (2); Met 1.03 (1); Ile 1.84 (2); Leu 4.47 (4); Tyr 0.91 (1); Phe 0.82 (1); 3-MeHis 1.09 (1); Lys 2.13 (2); Arg 3.26 (3). Confirmation of structure was provided by FAB mass spectroscopy. Calcd: $(M+H)^+$3389.0. Found: 3388.5.

EXAMPLE 4

Preparation of [His$^1$,Val$^2$,Ala$^{15}$,Leu$^{27}$]-GRF(1-32)-OH

Boc-Gly-PAM-resin (Bachem Inc., Torrance, Calif.) (0.7 g, 0.5 mmol) was charged into the reaction vessel of the Applied Biosystems Model 430A Peptide Synthesizer and subjected to 31 cycles of solid phase peptide synthesis to give 1.8 g of protected [His$^1$,Val$^2$,Ala$^{15}$Leu$^{27}$]-GRF(1-32)-PAM-resin. A 0.5 g portion was treated with HF and the resulting crude peptide (420 mg) was purified by HPLC as in Example 1 to give 34 mg of pure [His$^1$,Val$^2$,Ala$^{15}$,Leu$^{27}$]-GRF(1-32)-OH.

The product was shown to be homogeneous by analytical HPLC and gave the expected amino acid composition after acid hydrolysis (Hydrolysis: 6N HCl, 150° C., 1h): Asp 3.23 (3); Thr 0.94 (1); Ser 2.83 (3); Glu 4.23 (4); Gly 1.06 (1); Ala 3.06 (3); Leu 4.91 (5); Tyr 0.98 (1); His 0.93 (1); Lys 1.92 (2); Arg 3.22 (3). (6N HCl, 110° C., 72h): Val 2.01 (2); Ile 1.98 (2); Phe 1.00 (1). Confirmation of structure was provided by FAB mass spectroscopy. Calcd: $(M+H)^+$3671.2. Found: 3671.2.

EXAMPLE 5

Preparation of [His$^1$,Ile$^2$,Ala$^{15}$]-GRF(1-29)-NH$_2$

A 1 g portion of protected [Ala$^{15}$]-GRF(3-29)-BHA-resin was subjected to 2 cycles of solid phase peptide synthesis as in Example 1 to give 1.1 g of protected [His$^1$,Ile$^2$, Ala$^{15}$]-GRF(1-29)-BHA-resin. The protected peptide resin was cleaved with anhydrous HF to give 540 mg of crude peptide. The crude material (540 mg) was dissolved in 25 mL of 0.1% TFA/H$_2$O, filtered and loaded onto a Prep-Pak YMC-Basic column (4.8 cm×30 cm). The column was eluted with (A) H$_2$O (0.1% TFA)-(B) CH$_3$CN (0.1% TFA) in a linear gradient mode from 20%(B) to 50%(B) in 90 min. with a flow rate of 50 mL/min. Fractions were collected every 0.5 min. and analyzed by the analytical HPLC system. Fractions containing semi-pure product were combined, evaporated and lyophilized.

The semi-pure material was dissolved in 0.1% TFA/H$_2$O, centrifuged, filtered and loaded onto a 2.5×50 cm Nucleosil column. The column was eluted with (A) H$_2$O (0.1% TFA)-(B) CH$_3$CN (0.1% TFA) in a linear gradient mode from 25% (B) to 45% (B) in 90 min. with a flow rate of 10 mL/min. Fractions were collected (1 mL/fraction) and aliquots were analyzed by the analytical HPLC system. The product emerged in fractions 50-54 which were combined, evaporated and lyophilized to give pure [His$^1$,Ile$^2$, Ala$^{15}$]-GRF(1-29)-NH$_2$. Yield: 37 mg.

The product was shown to be homogenous by analytical HPLC and gave the expected amino acid composition after acid hydrolysis (6N HCl, 150° C., 1h): Asp 2.82 (3); Thr 0.95 (1); Ser 3.07 (3); Glu 2.02 (2); Ala 3.00 (3); Met 0.94 (1); Leu 3.71 (4); Tyr 0.97 (1); His 1.10 (1); (110°, 24h): Val 0.86 (1); Ile 2.46 (3); Phe 0.82 (1); Lys 1.92 (2); Arg 2.87 (3). Confirmation of structure was provided by FAB mass spectroscopy. Calcd: $(M+H)^+$3389.0. Found 3389.0.

EXAMPLE 6

Preparation of [Ile$^2$,Ala$^{15}$]-GRF(1-29)-NH$_2$

A 1 g portion of protected [Ala$^{15}$]-GRF(3-29)-BHA-resin was subjected to 2 cycles of solid phase peptide synthesis as in Example 1 to give 0.92 g of protected [Ile$^2$, Ala$^{15}$]-GRF (1-29)-BHA resin. An 0.5 g portion was cleaved with anhydrous HF to give 0.215 g of crude [Ile$^2$, Ala$^{15}$]-GRF (1-29)-NH$_2$. The crude product (0.215 g) was dissolved in 25 mL of 0.1% TFA/H$_2$O, centrifuged, filtered and loaded onto a 1×25 cm Nucleosil C-18 column. The column was eluted with (A) H$_2$O (0.1% TFA)-(B) CH$_3$CN(0.1% TFA) in a linear mode from 20% (B) to 45% (B) in 90 min. with a flow rate of 15 mL/min. Fractions were collected every min. and aliquots were analyzed by the analytical HPLC system. Fractions 48-49 (containing semi-pure product) were combined, evaporated and lyophilized. The semi-crude lyophilized product was dissolved in distilled water and loaded onto a Waters Phenyl Column (0.78×30 cm). The column was eluted with (A) H$_2$O (0.1% TFA)-(B) CH$_3$CN (0.1% TFA) in a linear mode going from 30% (B) to 50% (B) in 50 min. with a flow rate of 3 mL/min.

Fractions were analyzed by analytical HPLC and fraction 41 which contained pure product was evaporated and lyophilized to give 4 mg of product.

The product was shown to be homogenous by analytical HPLC and gave the expected amino acid composition after acid hydrolysis. (6N HCl, 150° C., 1h): Thr 0.95 (1); Ser 3.04 (3). (6N HCl, 110° C., 72h): Asp 2.86 (3); Glu 2.40 (2); Ala 3.00 (3); Val 1.11 (1); Met 1.04 (1); Ile 2.60 (3); Leu 4.57 (4); Tyr 1.60 (2); Phe 0.83 (1); Lys 2.39 (2); Arg 3.45

EXAMPLE 7

Preparation of [Leu$^2$,Ala$^{15}$]-GRF(1-29)-NH$_2$

A 1 g portion of protected [Ala$^{15}$]-GRF(3-29)-BHA-resin was subjected to 2 cycles of solid phase peptide synthesis as in Example 1 to give 1.1 g of protected [Leu$^2$, Ala$^{15}$]-GRF (1-29)-BHA-resin. The protected peptide resin (1.1 g) was cleaved with anhydrous HF to give 571 mg of crude peptide which was purified as in Example 1. A total of 34 mg of pure [Leu$^2$,Ala$^{15}$]-GRF(1-29)-NH$_2$ was obtained.

The product was shown to be homogeneous by analytical HPLC and gave the expected amino acid composition after acid hydrolysis (6N HCl, 150° C., 1h): Thr 0.94 (1); Ser 3.01 (3); Tyr 2.04 (2). (110° C., 24h): Asp 2.74 (3); Glu 2.03 (2); Ala 3.00 (3); Val 0.90 (1); Met 0.96 (1); Ile 1.80 (2); Leu 4.84 (5); Phe 0.86 (1); Lys 1.83 (2); Arg 2.96 (3). Confirmation of structure was provided by FAB mass spectroscopy. Calcd.: (M+H)$^+$3415.0. Found: 3415.5

EXAMPLE 8

Preparation of [desNH$_2$His$^1$,Val$^2$,Ala$^{15}$]-GRF(1-29)-NH$_2$

A 1 g portion of protected [Ala$^{15}$]-GRF(3-29)-BHA-resin (from Example 1) was subjected to 2 cycles of solid phase peptide synthesis to give 1 g of protected [desNH$_2$His$^1$,Val$^2$, Ala$^{15}$]-GRF(1-29)-BHA-resin. A 0.5 g portion was cleaved with anhydrous HF to give 240 mg of crude [desNH$_2$His$^1$, Val$^2$,Ala$^{15}$]-GRF(1-29)-NH$_2$. After purification (as in Example 7), using the Prep-Pak YMC-Basic HPLC column, a total of 19 mg of pure [desNH His$^1$,Val$^2$,Ala$^{15}$]-GRF(1-29)-NH$_2$ was obtained.

The product was shown to be homogenous by analytical HPLC and gave the expected amino acid composition after acid hydrolysis (6N HCl, 150° C., 1h): Asp 3.06 (3); Thr 0.94 (1); Ser 3.03 (3); Glu 2.22 (2); Ala 3.28 (3); Val 1.85 (2); Met 1.05 (1); Ile 1.93 (2); Leu 4.38 (4); Tyr 1.03 (1); Phe 0.90 (1); Lys 2.00 (2); Arg. 3.30 (3). Confirmation of structure was provided by FAB mass spectroscopy. Calcd: (M+H)$^+$3359.9. Found: 3359.9.

EXAMPLE 9

Preparation of [Val$^2$,Ala$^{15}$,Leu$^{27}$]-GRF(1-32)-OH

Boc-Gly-PAM-resin (10 g; 0.68 mmol/g) was placed in a 400 mL reaction vessel and solid phase peptide synthesis was carried out using a "shaker in the round" apparatus (Glas-Col Apparatus Co; Terre Haute, Ind.) for a total of 23 cycles to give protected [Ala$^{15}$,Leu$^{27}$]-GRF(9-29) PAM-resin (19.8 g). A portion of the protected peptide resin (10 g) was subjected to an additional 6 cycles of solid phase peptide synthesis to give 9.6 g of protected [Ala$^{15}$,Leu$^{27}$]-GRF(3-32)-PAM-resin. A 1 g portion of the protected [Ala$^{15}$,Leu$^{27}$]-GRF(3-32)-PAM-resin was finally subjected to 2 additional cycles of solid phase peptide synthesis to yield protected [Val$^2$,Ala$^{15}$, Leu$^{27}$]-GRF(3-32)-PAM-resin (1 g). The protected peptide resin was cleaved with anhydrous HF to yield 540 mg of crude [Val$^2$,Ala$^{15}$, Leu$^{27}$]-GRF (1-32)-OH.

The crude peptide mixture (540 mg) was purified by HPLC (as in Example 5) using the YMC-Prep Pak column and 15 mg of pure [Val$^2$,Ala$^{15}$,Leu$^{27}$]-GRF(1-32)-OH was obtained.

The product was shown to be homogeneous by analytical HPLC and gave the expected amino acid composition after acid hydrolysis (6N HCl; 150° C., 1h): Asp 2.98 (3); Thr 1.03 (1); Ser 2.96 (3); Glu 4.17 (4); Gly 1.09 (1); Ala 3.00 (3); Val 1.82 (2); Ile 1.83 (2); Leu 5.14 (5); Tyr 2.00 (2); Phe 0.74 (1); Lys 2.00 (2); Arg 3.09 (3). Confirmation of structure was provided by FAB mass spectroscopy. Calcd: (M+H)$^+$3696.3. Found: 3696.2

EXAMPLE 10

Synthesis of [His$^1$,Val$^2$,Ala$^{15}$,Leu$^{27}$, Asn$^{28}$]-GRF(1-32)-OH

Boc-Gly-PAM-resin can be charged into a reaction vessel of a peptide synthesizer and be subjected to 31 cycles of solid phase peptide synthesis to give the protected [His$^1$, Val$^2$,Ala$^{15}$,Leu$^{27}$,Asn$^{28}$]-GRF(1-32)-PAM-resin. The PAM-resin can be treated with HF as in Example 2 to yield crude [His$^1$,Val$^2$,Ala$^{15}$, Leu$^{27}$,Asn$^{28}$]-GRF(1-32)-OH. A portion of this crude product can then be subjected to HPLC purification as in Example 1. The desired product emerging in several fractions can be combined, evaporated and lyophilized. The product can be shown to be homogeneous by analytical HPLC and confirmed by amino acid analysis.

EXAMPLE 11

Synthesis of [His$^1$,Leu$^2$,Ala$^{15}$,Leu$^{27}$]-GRF(1-32)-OH

Boc-Gly-PAM-resin can be charged into a reaction vessel of a peptide synthesizer and be subjected to 31 cycles of solid phase peptide synthesis to give the protected [His$^1$, Leu$^2$,Ala$^{15}$,Leu$^{27}$]-GRF(1-32)-PAM-resin. The PAM-resin can be treated with HF as in Example 2 to yield crude [His$^1$,Leu$^2$, Ala$^{15}$,Leu$^{27}$]-GRF(1-32)-OH. A portion of this crude product can then be subjected to HPLC purification as in Example 1. The desired product emerging in several fractions can be combined, evaporated and lyophilized. The product can be shown to be homogeneous by analytical HPLC and confirmed by amino acid analysis.

EXAMPLE 12

Synthesis of [His$^1$,Ile$^2$,Ala$^{15}$,Leu$^{27}$]-GRF(1-32)-OH

Boc-Gly-PAM-resin can be charged into a reaction vessel of a peptide synthesizer and subjected to 31 cycles of solid phase peptide synthesis to give the protected [His$^1$, Ile$^2$, Ala$^{15}$,Leu$^{27}$]-GRF(1-32)-PAM-resin. The PAM-resin can be treated with HF as in Example 2 to yield crude [His$^1$,Ile$^2$, Ala$^{15}$,Leu$^{27}$]-GRF(1-32)-OH. A portion of this crude product can then be subjected to HPLC purification as in Example 1. The desired product emerging in several fractions can be combined, evaporated and lyophilized. The product can be shown to be homogeneous by analytical HPLC and confirmed by amino acid analysis.

EXAMPLE 13

Synthesis of [His$^1$,Val$^2$,Ala$^{15}$,Leu$^{27}$]-GRF(1-40)-OH

Boc-Ala-PAM-resin can be charged into a reaction vessel of a peptide synthesizer and subjected to 39 cycles of solid phase peptide synthesis to give the protected [His$^1$,Val$^2$, Ala$^{15}$,Leu$^{27}$]-GRF(1-40)-PAM-resin. The protected PAM-resin can be treated with HF as in Example 2 to yield crude [His$^1$,Val$^2$,Ala$^{15}$,Leu$^{27}$]-GRF(1-40)-OH. A portion of this crude product can then be subjected to HPLC purification as in Example 1. The desired product emerging in several fractions can be combined, evaporated and lyophilized. The product can be shown to be homogeneous by analytical HPLC and confirmed by amino acid analysis.

EXAMPLE 14

Synthesis of [His$^1$,Leu$^2$,Ala$^{15}$,Leu$^{27}$]-GRF (1-40)-OH

Boc-Ala-PAM-resin can be charged into a reaction vessel of a peptide synthesizer and subjected to 39 cycles of solid phase peptide synthesis to give the protected [His$^1$, Leu$^2$, Ala$^{15}$,Leu$^{27}$]-GRF(1-40)-PAM resin. The protected PAM-resin can be treated with HF as in Example 2 to yield crude [His$^1$,Leu$^2$,Ala$^{15}$,Leu$^{27}$]-GRF(1-40)-OH. A portion of this crude product can then be subjected to HPLC purification as in Example 1. The desired product emerging in several fractions can be combined, evaporated and lyophilized. The product can be shown to be homogeneous by analytical HPLC and confirmed by amino acid analysis.

EXAMPLE 15

Synthesis of [His$^1$,Ile$^2$,Ala$^{15}$,Leu$^{27}$]-GRF(1-40)-OH

Boc-Ala-PAM-resin can be charged into a reaction vessel of a peptide synthesizer and subjected to 39 cycles of solid phase peptide synthesis to give the protected [His$^1$, Ile$^2$, Ala$^{15}$,Leu$^{27}$]-GRF(1-40)-PAM-resin. The protected PAM-resin can be treated with HF as in Example 2 to yield crude [His$^1$,Ile$^2$,Ala$^{15}$,Leu$^{27}$]-GRF(1-40)-OH. A portion of this crude product can then be subjected to HPLC purification as in Example 1. The desired product emerging in several fractions can be combined, evaporated and lyophilized. The product can be shown to be homogeneous by analytical HPLC and confirmed by amino acid analysis.

EXAMPLE 16

The biological activity of the novel peptides were compared with that of a synthetic standard of the natural sequence of GRF(1-44)-NH$_2$ which was isolated from a human pancreatic tumor of an individual suffering from acromegaly (Salk Institute standard hp-GRF-NH$_2$(NL-A-10)). The assay for biological activity, which is based on the ability to stimulate production of growth hormone in rat pituitary cells in tissue culture, was performed in the following manner.

Pituitaries from 30-40 male Sprague-Dawley rats (175 g) were removed aseptically after decapitation. The anterior lobes were collected, washed 3 times in sterile Hepes buffer (0.025M)(pH 7.35) and dispersed at 37° C. in 20-30 ml Hepes buffer (pH 7.35) containing collagenasa (4 mg per ml) and Dispase (Protease grande II, 2 mg per ml). After gentle 80 min. vortexing and trituration by Pasteur pipette, the dispersed cells were separated by centrifugation (150×g, 4 min.) and re-suspended in Hepes buffer containing neuraminidase (4 µg/ml), and 200 µg/ml ethylenediamine-tetraacetic acid (EDTA) disodium salt pH 7.35, for 10 min. The cells were washed twice with plating medium and plated on multiwell-plates (1.5×10$^5$ cells per ml) using the following defined medium: F-12/DMEM/BGJ(6:3:1) (Gibco: 430-1700/430-1600/320-2591) with 2 g BSA/l., 2.38 g Hepes/l., 50 mg Gentamycin/1 (Schering Co.). The medium in each well was supplemented either with the novel peptide or natural GRF(1-44)-NH$_2$ at concentrations ranging from 3.1 to 200 fmol. per ml. of medium. Control wells contained no supplement. Plating was done with this medium added with 2% fetal calf serum to ensure rapid fixation of the cells. On the fourth day the cells were washed twice with the defined medium without fetal calf serum. Finally 900 µl of defined medium was added to each well plus 100 µl of the same medium containing each individual treatment, in triplicate. After 3 hours of incubation the medium was collected and diluted as required to conduct radioimmuno- assays (RIAs) for rat growth hormone. RIAs were conducted using Sinha's anti-murine GH immune serum and procedures according to the National Pituitary Agency using protein A to precipitate antibody antigen complex. The results are summarized in Table 1.

TABLE 1

| Potency of GRF Analogs Relative to GRF(1-44)-NH$_2$ | |
|---|---|
| GRF(1-29)-NH$_2$ | 0.71 |
| GRF(1-44)-NH$_2$ | 1.00 |
| [His$^1$,Ile$^2$,Ala$^{15}$]-GRF(1-29)-NH$_2$ | 1.24 |
| [desNH$_2$His$^1$,Val$^2$,Ala$^{15}$]-GRF(1-29)-NH$_2$ | 1.21 |
| [His$^1$,Val$^2$,Ala$^{15}$]-GRF(1-29)-NH$_2$ | 2.58 |
| [His$^1$,Val$^2$,Ala$^{15}$,Leu$^{27}$]-GRF(1-32)-OH | 2.40 |

In vitro plasma stability of GRF analogs were determined by porcine plasma incubation at 37° C. Pooled porcine plasma was collected from control pigs and stored at -20° C. GRF analogs of interest were prepared as discussed above. The plasma was first thawed and centrifuged at 3000 rpm for 20 minutes at 4° C. The plasma was then placed in a shaker bath at a temperature of 37° C. and allowed to equilibrate for 10 minutes. GRF analogs were dissolved in water containing 0.1% TFA at a concentration of 2 µg/µl. As soon as the initial equilibration was completed, an analog was added into the plasma sample to a final concentration of 100 µg/ml. Immediately after the addition of a GRF analog, a 1 ml aliquot of plasma sample was withdrawn and acidified with 0.2 ml of 0.1M TFA/H$_2$O and kept at 0° C. for later solid phase extraction. The remaining plasma samples were incubated in the water bath and 1 ml aliquots were withdrawn at different time periods and acidified by the same procedure described above.

Plasma samples were extracted with SEP-PAK octadecyl columns (Waters Associates). The column cartridge was washed with 2 ml 80% acetic acid followed by 4 ml of 0.01M TFA. After the plasma sample was loaded, the column was washed with 3 ml of 0.1M TFA to remove the excess unbound biological material. The solvent remaining in the cartridges was forced out by two passes of air from a 10 ml syringe. The bound material was then eluted with 80% acetic acid and 3 ml eluate was collected for chromatographic analysis. Two high performance liquid chromatography systems were used. System A: Instrumentation—Perkin-Elmer Series 4 liquid chromatography microprocessor-controlled solvent delivery system, Waters intelligent sample processor (WISP) model 710 (Waters Associates), and a Hewlett-Packard 1040M Diode Assay Detection System. Column—Delta Pak C18, 3.5×150 mm, 5 µm spherical (Nihon Waters Ltd.). Mobile phase-(A) 0.1% TFA in H$_2$O, (B) 0.1% TFA in 95% acetonitrile and 5% H$_2$O. Gradient was 34-50% (B) in 60 minutes, flow rate 1 ml/minute, and the detection was at 215 nm. System B: Instrumentation—Waters 600 multi-solvent delivery system, WISP model 712 and LDC spectromonitor III. Column—Vydac 201TP54, C18 4.6×250 mm, 10 µm (The Separations Group). Mobile phase—same as in System A. Gradient max 30% (B) isocratic for 10 minutes, followed by 30-50% (B) gradient for 60 minutes, flow rate was 1 ml/minute, and the detection was at 215 nm. Amino acid analysis was done as described above. Results of plasma half life are found in Table 2.

TABLE 2

Plasma Stability of Modified GRF Analogs

| Compound | Half Life ($t_{1/2}$), minutes |
|---|---|
| GRF(1-29)-NH$_2$ | 13 |
| [Ala$^{15}$]-GRF(1-29)-NH$_2$ | 17 |
| [His$^1$,Val$^2$,Ala$^{15}$]-GRF(1-29)-NH$_2$ | 60 |
| [His$^1$,Val$^2$,Ala$^{15}$,Leu$^{27}$]-GRF(1-32)-OH | 60 |
| [Val$^2$,Ala$^{15}$,Leu$^{27}$]-GRF(1-32)-OH | 70 |

What is claimed is:

1. A compound of the formula

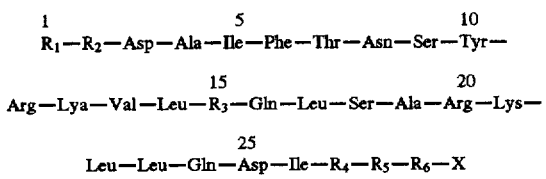

wherein R$_1$ is His, 3-MeHis, desNH$_2$His, Tyr, or desNH$_2$Tyr; R$_2$ is Val; R$_3$ is Ala; R$_4$ is Met, Leu, Ile, or Nle; R$_5$ is Ser or Asn; R$_6$ is an amino acid sequence Arg-Gln-Gln-Gly-Glu-Ser-Asn-Gln-Glu-Arg-Gly-Ala-Arg-Ala-Arg-Leu or fragments thereof where the fragment is reduced in number by one to fifteen amino acid residues from the amino acid residue which carries substituent X; and X is either OH or NH$_2$, and the pharmaceutically acceptable acid or base addition salts thereof.

2. A compound of claim 1, wherein R$_3$ is Ala and R$_6$ is Arg.

3. A compound of claim 2, which is [His$^1$,Val$^2$, Ala$^{15}$]-GRF(1-29)-NH$_2$.

4. A compound of claim 2, which is [3-MeHis$^1$, Val$^2$, Ala$^{15}$]-GRF(1-29)-NH$_2$.

5. A compound of claim 2, which is [desNH$_2$His$^1$, Val$^2$, Ala$^{15}$]-GRF(1-29)-NH$_2$.

6. A compound of claim 1, wherein R$_3$ is Ala and R$_6$ is Arg-Gln-Gln-Gly.

7. A compound of claim 6, which is [His$^1$,Val$^2$, Ala$^{15}$, Leu$^{27}$]-GRF(1-32)-OH.

8. A compound of claim 6, which is [Val$^2$,Ala$^{15}$, Leu$^{27}$]-GRF(1-32)-OH.

9. A compound of claim 6, which is [His$^1$,Val$^2$, Ala$^{15}$, Leu$^{27}$,Asn$^{28}$]-GRF(1-32)-OH.

10. A compound of claim 1, wherein R$_3$ is Ala and R$_6$ is Arg-Gln-Gln-Gly-Glu-Ser-Asn-Gln-Glu-Arg-Gly-Ala.

11. A compound of claim 10, which is [His$^1$,Val$^2$, Ala$^{15}$, Leu$^{27}$]-GRF(1-40)-OH.

12. A pharmaceutical composition for stimulating the release of growth hormone in warm and cold-blooded animals comprising a compound of the formula

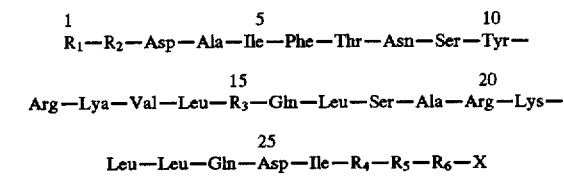

wherein R$_1$ is His, 3-MeHis, desNH$_2$His, Tyr, or desNH$_2$Tyr; R$_2$ is Val, R$_3$ is Ala; R$_4$ is Met, Leu, Ile, or Nle; R$_5$ is Ser or Asn; R$_6$ is an amino acid sequence selected from Arg-Gln-Gln-Gly-Glu-Ser-Asn-Gln-Glu-Arg-Gly-Ala-Arg-Ala-Arg-Leu or fragments thereof where the fragment is reduced in number by one to fifteen amino acid residues from the amino acid residue which carries substituent X; and X is either OH or NH$_2$, or the pharmaceutically acceptable acid or base addition salts thereof, and a pharmaceutically acceptable carrier.

13. A method of treating growth related disorders' characterized by growth hormone deficiencies or for improvement of growth performance in warm and cold-blooded animals comprising administering to said animal a compound of the formula

wherein R$_1$ is His, 3-MeHis, desNH$_2$His, Tyr, or desNH$_2$Tyr; R$_2$ is Val; R$_3$ is Ala; R$_4$ is Met, Leu, Ile, or Nle; R$_5$ is Ser or Asn; R$_6$ is an amino acid sequence selected from Arg-Gln-Gln-Gly-Glu-Ser-Asn-Gln-Glu-Arg-Gly-Ala-Arg-Ala-Arg-Leu or fragments thereof where the fragment is reduced in number by one to fifteen amino acid residues from the amino acid residue which carries substituent X; and X is either OH or NH$_2$, or a pharmaceutically acceptable acid or base addition salt thereof, which is effective in treating growth hormone related disorders characterized by growth hormone deficiencies or for improvement of growth performance in warm or cold-blooded animals.

* * * * *

UNITED STATES PATENT AND TRADEMARK OFFICE
CERTIFICATE OF CORRECTION

PATENT NO. : 5,696,089
DATED : December 9, 1997
INVENTOR(S) : Arthur Martin Felix and Edgar Philip Heimer It is certified that error appears in the above-indentified patent and that said Letters Patent is hereby corrected as shown below:

In claim 1, column 15, line 19, delete "-Lya-" and insert therefor -- -Lys- --.

In claim 12, column 16, line 9, delete "-Lya-" and insert therefor -- -Lys- --.

In claim 12, column 16, line 14, delete "Val," and insert therefor -- Val; --.

In claim 13, column 16, line 25, delete "disorders'" and insert therefor -- disorders --.

In claim 13, column 16, delete lines 30-35 and insert the following:

$$\begin{array}{c} 1 \quad\quad\quad 5 \quad\quad\quad\quad\quad 10 \\ R_1-R_2-Asp-Ala-Ile-Phe-Thr-Asn-Ser-Tyr- \\ 15 \quad\quad\quad\quad 20 \\ Arg-Lys-Val-Leu-R_3-Gln-Leu-Ser-Ala-Arg-Lys- \\ 25 \\ Leu-Leu-Gln-Asp-Ile-R_4-R_5-R_6-X \end{array}$$

--.

Signed and Sealed this

Twenty-fourth Day of February, 1998

Attest:

BRUCE LEHMAN

Attesting Officer        Commissioner of Patents and Trademarks